United States Patent [19]

Matsuzawa et al.

[11] 4,042,625
[45] Aug. 16, 1977

[54] PROCESS AND CATALYST FOR PREPARING UNSATURATED CARBOXYLIC ACID

[75] Inventors: Hideo Matsuzawa; Masato Otani; Hiromichi Ishii, all of Ohotake; Kantaro Yamada, Yokohama; Hasao Kobayashi, Ohotake, all of Japan

[73] Assignee: Mitsubishi Rayon Company, Ltd., Tokyo, Japan

[21] Appl. No.: 590,505

[22] Filed: June 25, 1975

[30] Foreign Application Priority Data

July 3, 1974 Japan ................... 49-76593

[51] Int. Cl.$^2$ ............... C07C 51/24; B01J 27/02; B01J 27/14
[52] U.S. Cl. .................. 260/530 N; 252/435; 252/437
[58] Field of Search ............... 252/435, 437; 260/530 N

[56] References Cited

U.S. PATENT DOCUMENTS

| 3,086,026 | 4/1963 | Wiebusch | 252/435 X |
| 3,795,703 | 3/1974 | Niina | 252/435 X |
| 3,875,220 | 4/1975 | White | 260/430 N |
| 3,893,945 | 7/1975 | Kobayashi | 252/435 |

OTHER PUBLICATIONS

Derwent Publication DT 2454-587.
Derwent Publication DT 2455-216.

Primary Examiner—Winston A. Douglas
Assistant Examiner—John F. Niebling
Attorney, Agent, or Firm—Oblon, Fisher, Spivak, McClelland & Maier

[57] ABSTRACT

Acrylic acid or methacrylic acid is prepared by vapor-phase catalytic oxidation of acrolein or methacrolein, with molecular oxygen at a temperature of from 240° to 450° C in the presence of a catalyst represented by the formula:

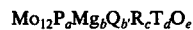

$$Mo_{12}P_aMg_bQ_{b'}R_cT_dO_e$$

wherein Mo is molybdenum, P is phosphorus, Mg magnesium, O is oxygen, Q is at least one of calcium, strontium, and barium, R is at least one of potassium, rubidium, cesium and thallium, T is at least one of vanadium, tungsten and nickel, and $a$, $b$, $c$, $d$, and $e$ are atomic ratios of the respective elements, where $a=0.5-6$, $b=0.2-6$, $b+b' = 0.2-6$, $b'$ ranges from 0 to a value determined by the magnesium content of the catalyst and the limits of $b+b'$, $c=0.2-6$, $d=0-6$, and $e$ is a value dependent upon the oxidation state of the catalyst.

7 Claims, No Drawings

PROCESS AND CATALYST FOR PREPARING UNSATURATED CARBOXYLIC ACID

BACKGROUND OF THE INVENTION

1. Field of the Invention

This invention relates to a process for preparing an unsaturated carboxylic acid by vapor-phase catalytic oxidation of the corresponding unsaturated aldehyde with molecular oxygen, and more particularly to a process for preparing acrylic acid or methacrylic acid from acrolein or methacrolein, using a catalyst comprising phosphorus, molybdenum, oxygen, magnesium and optionally at least one of Ca, Sr, and Ba, and at least one of V, W and Ni as an optional component.

2. Description of the Prior Art

Heretofore, many processes have been proposed for preparing unsaturated carboxylic acids from the corresponding unsaturated aldelydes. For example, Japanese Patent Publication No. 12129/69 discloses a process for preparing acrylic acid from acrolein, using a catalyst consisting of Mo, V, W and silica, Japanese Patent Publication No. 19260/63 a process for preparing acrylic acid, using a catalyst consisting of P, Mo and As, etc.

Many processes have been proposed for preparing methacrylic acid. For example, Japense Patent Publication No. 6605/72 discloses a process based on a catalyst consisting of Mo, Ni and Ti, Japanese Patent Publication No. 10773/73 a process based on a catalyst containing Mo and Ti, etc. Furthermore, U.S. Pat. Nos. 3,686,294 and 3,761,516 disclose processes for preparing methacrylic acid, based on a catalyst of P-Mo-As type, U.S. Pat. No. 3,795,703 a process based on a catalyst of P-Mo-alkali metal type, and Belgian Pat. No. 817,100 a process based on a catalyst of P-Mo-Sb-Zn type.

The catalysts disclosed in these publications and patents have their respective advantages, but from the industrial viewpoint they have disadvantages in selectivity or catalyst life.

SUMMARY OF THE INVENTION

An object of the present invention is to provide a catalyst having a long catalyst life, applicable to a process for preparing an unsaturated carboxylic acid from the corresponding unsaturated aldehyde in high yield.

According to the present invention, a process for preparing acrylic acid or methacrylic acid is provided, which is characterized by vapor-phase catalytic oxidation of acrolein or methacrolein, at a temperature of from 240° to 450° C in the presence of a catalyst represented by the following formula:

$$Mo_{12}P_aMg_bQ_{b'}R_cT_dO_e$$

wherein Mo represents molybdenum, P phosphorus, Mg magnesium, O oxygen, Q at least one of Ca, Sr and Ba, R at least one of K, Rb, Cs and Tl, T at least one of V, W and Ni, and $a$, $b$, $c$, $d$, are $e$ are atomic ratios of the respective elements, wherein $a = 0.5 - 6$, $b = 0.2 - 6$, $b + b' = 0.2 - 6$, $b'$ ranges from 0 to a value determined by the magnesium content of the catalyst and the limits of $b + b'$, $c = 0.2 - 6$, $d = 0 - 6$, preferably $d = 0.1 - 4$, and $e$ is a value dependent upon the oxidation state of the catalyst.

DESCRIPTION OF THE PREFERRED EMBODIMENTS

In the catalyst to be used in the present invention, the existing states of phosphorus, molybdenum and other added metals are complicated, and have not yet been fully clarified in the strict sense. It seems clear, however, that they are not based on a mere mixture of the respective metal oxides. It seems that they are based on complexes of the respective metals that are tightly bound through oxygen.

It is well known that catalyst systems containing phosphorus and molybdenum are effective for gas phase oxidation of acrolein or methacrolein, but phosphorus and molybdenum form very complicated compounds, depending upon their mixing ratio, and heat-treating temperature and atmosphere. Therefore, when a catalyst system containing phosphorus and molybdenum is used in the gas phase oxidation, the catalyst structure will often change with time within the usually employed range of reaction temperatures, resulting in decrease in its activity and selectivity.

In the catalyst of the present invention, certain metals are added which have the property of forming very stable salts with phosphorus and molybdenum, and it seems that this property contributes to the maintenance of the catalyst activity and selectivity.

In the present invention, any conventional procedure can be employed for preparing the catalyst. For example, the catalyst can be prepared by the well known procedures of evaporation to dryness, precipitation, oxide mixing, etc. That is, the catalyst can be prepared, for example, by adding potassium nitrate to an aqueous solution of ammonium molybdate, adding thereto phosphoric acid and then an aqueous solution of barium nitrate, and evaporating the resulting mixed solution to dryness, or mixing powdered molybdenic acid, potassium phosphate and magnesium oxide, or adding phosphoric acid, and aqueous solution of cesium nitrate and an aqueous solution of strontium nitrate to an aqueous solution of phosphomolybdenic acid, and shaping the mixture resulting from any of these procedures. The shaped mixture, is then heat treated, or the mixture is heat treated and then shaped.

The catalyst components can be supported on, or diluted with, any of the well known inert carriers such as silica, alumina, silica-alumina, silicon-carbide, titanium oxide, tin dioxide, or the like.

The following raw materials can be used for the respective elements of the catalyst, for example, molybdenum trioxide, molybdic acid, ammonium molybdate, phospho-molybdic acid, or the like can be used as the raw materials for molybdenum. Phosphoric acid, phosphorus pentoxide, phospho-molybdic acid, phosphates, etc. can be used as the raw materials for phosphorus.

Other added metals represented by Q, R and T in the above general formula, can be used in the form of their nitrates, chlorides, phosphates, oxides, carbonates, ammonium salts, etc., for example, magnesium nitrate, calcium nitrate, barium chloride, strontium nitrate, potassium hydroxide, potassium nitrate, cesium carbonate, thallous nitrate, nickel nitrate, ammonium metavanadate, ammonium tungstate, etc. Other raw materials can be changed to oxides by thermal decomposition, hydrolysis, oxidation, etc, can also be used in addition to those described above.

In the catalyst of the present invention, it is preferred to use magnesium, or a combination of magnesium with calcium, strontium, or barium, wherein Q is defined as Ca, Ba and Sr. In the generic formula of the catalyst of the present invention, i.e. $Mo_{12}P_aMg_bQ_{b'}R_cT_dO_e$, the atomic ratio of Mg, i.e., $b$, can vary within the range of 0.2-6.0. Moreover, the total atomic ratio of the magnesium, calcium, strontium and barium components of the catalyst and thus the value of $b+b'$ to be selected so as to fall within the range of 0.2-6. Since component Q is optional, the value of $b'$ can range from 0 to a value determined by the magnesium content of the catalyst and the limits $b+b'$. As for component R, a combination of potassium with cesium is particularly preferred. It is preferable that both the atomic ratios total within the range of 0.5-5.

The heat-treating temperature of the catalyst may be 300° - 650° C, preferably 350° - 600° C. The heat-treating time will depend upon temperature, but an appropriate heat-treating time may be in a range of 1 hour to several tens of hours. Shaping or supporting a carrier can be carried out before or after calcination. In the present invention, acrolein or methacrolein is used as a starting material, but a mixture of acrolein and methacrolein can also be used. The present invention is especially suitable for oxidation of methacrolein.

The reactant unsaturated aldehyde can contain a small amount of impurities, such as water, lower carbon number saturated aldehydes, lower carbon number hydrocarbons, etc, and these impurities give no influence upon the reaction.

Concentration of the unsaturated aldehyde in the feed gas can be varied over a wide range, but is preferably 1 to 20% by volume, particularly preferably 3 to 10% by volume.

As an oxygen source, it is economical to use air, but air enriched with oxygen can also be used, if desired. The molar ratio of oxygen to unsaturated aldehyde in the feed gas is 0.3 to 4, preferably 0.4 to 2.5

The feed gas can be diluted with an inert gas, such as nitrogen, steam, carbon dioxide, or the like. In the practice of this reaction, it is preferable to prevent the feed gas from an exposure to elevated temperature at the locations not in contact with the catalyst layer.

Preferable reaction pressures range from atmospheric to several atmospheres. Reaction temperatures can be selected within the range of 240° to 450° C, but the preferably the reaction temperature is from 260° to 400° C. The gas space velocity will depend upon the reaction pressure and reaction temperature but can be selected within the range of 300 to 10,000 hr.$^{-1}$.

Having now generally described the invention, a more complete understanding can be attained be reference to certain specific examples which are included herein for purposes of illustration only and are not intended to be construed as limiting of the invention unless otherwise so specified. In the examples all parts are intended to mean parts by weight.

Unsaturated carboxylic acid selectivity is a percent ratio by mole of formed unsaturated carboxylic acid to reacted unsaturated aldehyde.

Reaction time means the time elapsing from the starting time set by the reaction conditions described therein.

EXAMPLE 1

In 200 parts of pure water at 60° C was dissolved 42.4 parts of ammonium paramolybdate. Thereto was added 4.04 parts of potassium nitrate and 2.3 parts of 85% phosphoric acid. Further, 2.61 part of barium nitrate dissolved in 50 parts of pure water heating was added thereto. The resulting solution mixture was heated with stirring and evaporated to dryness. The resulting cake was dried at 130° C for about 16 hours, and then disintegrated and calcined in air at 500° C for 4 hours. After the calcination, the product was pulverized, and shaped by compression with an addition of a small amount of graphite, whereby a catalyst having a composition in atomic ratios $Mo_{12}$, $P_1Ba_{0.5}K_2$, was prepared.

The resulting catalyst was filled in a reactor and a gas mixture consisting of 5% by volume of methacrolein, 10% by volume of oxygen, 30% by volume of steam and 55% by volume of nitrogen was passed through a catalyst layer at a reaction temperature 350° C at a space velocity of 1000 hr$^{-1}$. The products were collected, and analyzed by gas chromatography. It was found that 78.6% of methacrolein was reacted, and methyacrylic acid selectivity was 78.0%. In addition, acetic acid, carbon dioxide, carbon monoxide, etc. were formed. The reaction was continued under the same conditions for about 1,600 hours, but conversion of 78.5% and selectivity of 78.2% could be maintained throughout the reaction.

EXAMPLE 2

A gas mixture consisting of 5% by volume of acrolein, 10% by volume of oxygen, 30% by volume of steam, and 55% by volume of nitrogen was subjected to reaction at a reaction temperature of 360° C at a space Velocity of 1000 hr$^{-1}$, using the catalyst of Example 1, and the results are shown in Table 1.

Table I

| Ex. No. | Catalyst composition (atomic ratio) | Feed aldehyde | Reaction time (hr) | Reaction temperature (°C) | Conversion (%) | Selectivity (%) |
|---|---|---|---|---|---|---|
| 2 | $Mo_{12} P_1 Ba_{0.5}K_2$ | acrolein | 4 | 360 | 89.2 | 87.8 |
|   |   |   | 1600 | 360 | 89.0 | 87.9 |

EXAMPLES 3-6

Catalysts were prepared in the same manner as in Example 1, except that 5.90 parts of rubidium nitrate, 7.80 parts of cesium nitrate, and 10.7 parts thallous nitrate were used in place of potassium nitrate, and subjected to reaction under the same reaction conditions as in Example 1 or 2 except that the reaction temperature indicated in Table 2 was used. Results are shown in Table 2.

Table 2

| Ex. No. | Catalyst composition (atomic ratio) | Feed aldehyde | Reaction time (hr) | Reaction temperature (°C) | Conversion (%) | Selectivity (%) |
|---|---|---|---|---|---|---|
| 3 | $Mo_{12} P_1 Ba_{0.5} Rb_2$ | acrolein | 4 | 365 | 86.4 | 85.9 |
|   |   |   | 1,600 | 365 | 86.3 | 86.0 |
| 4 | $Mo_{12} P_1 Ba_{0.5} Rb_2$ | methacrolein | 4 | 355 | 78.8 | 76.6 |

Table 2-continued

| Ex. No. | Catalyst composition (atomic ratio) | Feed aldehyde | Reaction time (hr) | Reaction temperature (°C) | Conversion (%) | Selectivity (%) |
| --- | --- | --- | --- | --- | --- | --- |
|   |   |   | 1,600 | 355 | 78.8 | 76.6 |
| 5 | $Mo_{12}P_1Ba_{0.5}Cs_2$ | methacrolein | 4 | 355 | 80.6 | 84.2 |
|   |   |   | 1,600 | 355 | 80.5 | 84.0 |
| 6 | $Mo_{12}P_1Ba_{0.5}Tl_2$ | methacrolein | 4 | 345 | 80.1 | 82.8 |
|   |   |   | 1,600 | 345 | 80.0 | 82.0 |

EXAMPLE 7

In 200 parts of pure water was dissolved 47.0 parts of phosphomolybdic acid, and 2.30 parts of 85% phosphoric acid was added thereto. Then, 4.04 parts of potassium nitrate and 5.13 parts of magnesium nitrate, dissolved in 100 parts of pure water, were added to the resulting solution. The thus obtained solution mixture was heated with stirring, and evaporated to dryness. The resulting cake was dried at 130° C for about 16 hours, then disintegrated, shaped by compression, and calcined at 520° C for 3 hours, whereby a catalyst having a composition in atomic ratio, $Mo_{12}P_2Mg_1K_2$, was obtained.

The thus prepared catalyst was subjected to reaction under the same conditions as in Example 1, except that the reaction temperature of 355° C was used. Results are shown in Table 3.

Table 3

| Ex. No. | Catalyst Composition (atomic ratio) | Feed aldehyde | Reaction time (hr) | Reaction temperature (°C) | Conversion (%) | Selectivity (%) |
| --- | --- | --- | --- | --- | --- | --- |
| 7 | $Mo_{12}P_2Ml K_2$ | methacrolein | 4 | 355 | 75.5 | 78.4 |
|   |   |   | 1,600 | 355 | 75.4 | 79.0 |

EXAMPLES 3 – 9

Catalysts were prepared in the same manner as in Example 7, except that 3.28 parts of calcium nitrate or 5.67 parts of strontium nitrate was used in place of magnesium nitrate, and subjected to reaction under the same conditions as in Example 1, except that temperatures of 355° C or 360° C was used. Results are shown in Table 4.

Table 4

| Ex. No. | Catalyst Composition (atomic ratio) | Feed aldehyde | Reaction time (hr) | Reaction temperature (°C) | Conversion (%) | Selectivity (%) |
| --- | --- | --- | --- | --- | --- | --- |
| 8 | $Mo_{12}P_2Ca_1K_2$ | methacrolein | 4 | 355 | 74.3 | 77.9 |
|   |   |   | 1,600 | 355 | 74.3 | 78.1 |
| 9 | $Mo_{12}P_2Sr_1K_2$ | methacrolein | 4 | 360 | 75.2 | 75.5 |
|   |   |   | 1,600 | 360 | 75.3 | 75.7 |

EXAMPLES 10-12

Catalysts were prepared in the same manner as in Example 7, except that 3.28 parts of calcium nitrate, 5.67 parts of strontium nitrate or 5.22 parts of barium nitrate was used in addition to potassium nitrate and magnesium nitrate, and subjected to reaction under the same conditions as in Example 1, where a temperature of 345° C was employed. Results are shown in Table 5.

Table 5

| Ex. No. | Catalyst Composition (atomic ratio) | Feed aldehyde | Reaction time (hr) | Reaction temperature (°C) | Conversion (%) | Selectivity (%) |
| --- | --- | --- | --- | --- | --- | --- |
| 10 | $Mo_{12}P_2Mg_1Ca_1K_2$ | methacrolein | 4 | 350 | 76.3 | 80.3 |
|   |   |   | 1,600 | 350 | 76.3 | 80.5 |
| 11 | $Mo_{12}P_2Mg_1Sr_1K_2$ | methacrolein | 4 | 345 | 77.4 | 79.8 |
|   |   |   | 1,600 | 345 | 77.4 | 80.1 |
| 12 | $Mo_{12}P_2Mg_1Ba_1K_2$ | methacrolein | 4 | 345 | 76.7 | 80.2 |
|   |   |   | 1,600 | 345 | 76.5 | 80.4 |

EXAMPLES 13-14

Catalyst was prepared in the same manner as in Example 1, except that the amounts of phosphoric acid, potassium nitrate and barium nitrate were changed, and 3.90 parts of cesium nitrate was additionally used, and the catalyst composition was given by $P_3Mo_{12}Ba_1Cs_1K_1$.

The catalyst was subjected to reaction under the same conditions as in Example 1 or 2, and results are given in Table 6.

Table 6

| Ex. No. | Catalyst Composition (atomic ratio) | Feed aldehyde | Reaction time (hr) | Reaction temperature (°C) | Conversion (%) | Selectivity (%) |
|---|---|---|---|---|---|---|
| 13 | $Mo_{12} P_3 Ba_1 Cs_1 K_1$ | metha-crolein | 4 | 350 | 80.3 | 85.0 |
|  |  |  | 1,600 | 350 | 80.7 | 85.2 |
| 14 | " | " | 4 | 360 | 90.7 | 91.9 |
|  |  |  | 1,600 | 360 | 91.0 | 92.0 |

EXAMPLES 15–18

4 catalysts were prepared in the same manner as in Example 1, except that 1.17 parts of ammonium metavanadate, or 2.70 parts of ammonium tungstate, or 5.82 parts of nickel nitrate, or 1.17 parts of ammonium metavanadate and 2.70 parts of ammonium tungstate was additionally added thereto, and subjected to reaction under the same conditions as in Example, where reaction temperatures of 330° C, 335° C and 340° C were used. The results are shown in Table 7.

Table 7

| Ex. No. | Catalyst Composition (atomic ratio) | Feed aldehyde | Reaction time (hr) | Reaction temperature (°C) | Conversion (%) | Selectivity (%) |
|---|---|---|---|---|---|---|
| 15 | $Mo_{12} P_1 Ba_{0.5} K_2 V_{0.5}$ | metha-crolein | 4 | 340 | 79.5 | 80.0 |
|  |  |  | 1,600 | 340 | 79.7 | 79.9 |
| 16 | $Mo_{12} P_1 Ba_{0.5} K_2 W_{0.5}$ | " | 4 | 340 | 78.5 | 80.2 |
|  |  |  | 1,600 | 340 | 78.4 | 80.3 |
| 17 | $Mo_{12} P_1 Ba_{0.5} K_2 Ni_1$ | " | 4 | 335 | 79.0 | 80.1 |
|  |  |  | 1,600 | 335 | 79.2 | 79.8 |
| 18 | $Mo_{12} P_1 Ba_{0.5} K_2 V_{0.5} W_{0.5}$ | " | 4 | 330 | 80.1 | 80.0 |
|  |  |  | 1,600 | 330 | 80.0 | 80.3 |

COMPARATIVE EXAMPLES 1–2

Catalysts were prepared in the same manner as in Example 1, except that barium nitrate or potassium nitrate was not used, and subjected to reaction under the same conditions as in Example 1, where a reaction temperature of 400° C was used. Results are shown in Table 8.

Table 8

| Comp. Ex. No. | Catalyst Composition (atomic ratio) | Feed aldehyde | Reaction time (hr) | Reaction temperature (°C) | Conversion (%) | Selectivity (%) |
|---|---|---|---|---|---|---|
| 1 | $Mo_{12} P_1 Ba_{0.5}$ | methacro-lein | 4 | 400 | 40.7 | 60.5 |
| 2 | $Mo_{12} P_1 K_1$ | " | 4 | 400 | 51.7 | 62.8 |

Obviously, numerous additional modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. In a process for preparing acrylic acid or methacrylic acid by the vapor-phase catalytic oxidation of the corresponding unsaturated aldehyde with molecular oxygen at a temperature of from 240° – 450° C, the improvement comprising:

reacting said unsaturated aldehyde over a catalyst consisting essentially of molybdenum, phosphorus, magnesium, element Q, element R, element T and oxygen represented by the formula:

$Mo_{12} P_a Mg_b Q_{b'} R_c T_d O_e$ wherein Mo is molybdenum, P is phosphorus, Mg is magnesium, O is oxygen, Q is at least one metal selected from the group consisting of calcium, strontium and barium, R is at least one metal selected from the group consisting of potassium, rubidium, cesium and thallium, T is at least one metal selected from the group consisting of vanadium, tungsten and nickel, $a$, $b$, $b'$, $c$, $d$ and $e$ are atomic ratios of the respective elements, wherein $a = 0.5$–6, $b = 0.2$–6, $b + b' = 0.2$–6, $b'$ ranges from 0 to a value determined by the magnesium content of the catalyst and the limits of $b + b'$, $c = 0.2$–6, $d = 0$–6, and $e$ is a value dependent upon the oxidation state of the catalyst.

2. The process according to claim 1, wherein the catalyst contains a combination of magnesium and at least one metal selected from the group consisting of calcium, strontium and barium, such that the sum of the respective atomic ratios is 0.2–6.

3. The process according to claim 1, wherein R is a combination of potassium and cesium, and sum of atomic ratios thereof is 0.2–5.

4. The process according to claim 1, wherein $d$ is 0.1–4.

5. A catalyst for preparing acrylic acid or methacrylic acid by the vapor phase catalytic oxidation of a corresponding unsaturated aldehyde with molecular oxygen at a temperature of from 240°–450° C, which comprises: a composition of the formula:

$Mo_{12} P_a Mg_b Q_{b'} R_c T_d O_e$ wherein Mo is molybdenum, P is phosphorus, Mg is magnesium, O is oxygen, Q is at least one metal selected from the group consisting of calcium, strontium and barium, R is at least one metal selected from the group consisting of potassium, rubidium, cesium and thallium, T is at least one metal selected from the group consisting of vanadium, tungsten and nickel, $a$, $b$, $b'$, $c$, $d$ and $e$ are atomic ratios of the respective elements, wherein $a$ = 0.5–6, $b$=0.2–6, $b + b'$=0.2–6, $b'$ ranges from 0 to a value determined by the magnesium content of the catalyst and the limits of $b + b'$, $c$=0.2–6, $d$=0–6 and $e$ is a value dependent upon the oxidation state of the catalyst.

6. The catalyst of claim 5, wherein said catalyst contains a combination of magnesium and at least one metal selected from the group consisting of calcium, strontium and barium such that the sum of the respective atomic ratio is 0.2–6.

7. The catalyst of claim 5, wherein $d$ is 0.1–4.

UNITED STATES PATENT AND TRADEMARK OFFICE
CERTIFICATE OF CORRECTION

PATENT NO. : 4,042,625
DATED : August 16, 1977
INVENTOR(S) : Hideo Matsuzawa et al It is certified that error appears in the above—identified patent and that said Letters Patent are hereby corrected as shown below:

Please delete:

"[75] Inventors: Hideo Matsuzawa; Masato Otani; Hiromichi Ishii, all of Ohotake; Kantaro Yamada, Yokohama; Hasao Kobayashi, Ohotake, all of Japan"

and insert therefor:

--[75] Inventors: Hideo Matsuzawa; Masato Otani; Hiromichi Ishii, all of Ohotake; Kantaro Yamada, Yokohama; Masao Kobayashi, Ohotake, all of Japan--

Signed and Sealed this

Fourteenth Day of February 1978

[SEAL]

Attest:

RUTH C. MASON
*Attesting Officer*

LUTRELLE F. PARKER
*Acting Commissioner of Patents and Trademarks*